United States Patent [19]

Goldman

[11] Patent Number: 5,317,040
[45] Date of Patent: May 31, 1994

[54] METHOD FOR THE TREATMENT OF PERTUSSIS WITH AMINOGUANIDINE

[75] Inventor: William E. Goldman, St. Louis, Mo.

[73] Assignee: Washington University, St Louis, Mo.

[21] Appl. No.: 8,948

[22] Filed: Jan. 26, 1993

[51] Int. Cl.$^5$ ............................................. A61K 31/155
[52] U.S. Cl. ................................................... 514/634
[58] Field of Search .......................... 514/634; 424/92

[56] References Cited

U.S. PATENT DOCUMENTS

| | | | |
|---|---|---|---|
| 4,704,274 | 11/1987 | Sakuma et al. | 424/88 |
| 5,077,313 | 12/1991 | Lubec | 514/565 |
| 5,128,360 | 7/1992 | Cerami et al. | 514/400 |
| 5,132,453 | 7/1992 | Griffith | 562/560 |
| 5,158,883 | 10/1992 | Griffith | 435/240.2 |
| 5,196,450 | 3/1993 | Sjoerdsma et al. | 514/565 |

OTHER PUBLICATIONS

Goldman et al., Infect. Immun. 36, 782–794 (1982).
Cookson et al., Infect. Immun. 57, 2223–2229 (1989).
Cookson et al., Biochemistry 28, 1744–1749 (1989).
Corbett et al., Diabetes 41, 552–556 (1992).
Goldman and Baseman, In Vitro 16, 313–319 (1980).
Green et al., Anal. Biochem. 126, 131–138 (1982).
The Merck Manual, Fourteenth Edition, pp. 1897–1899 (1982).

*Primary Examiner*—Frederick E. Waddell
*Assistant Examiner*—T. J. Criares
*Attorney, Agent, or Firm*—Scott J. Meyer

[57] ABSTRACT

A method for the treatment of pertussis is disclosed which comprises administering a selective inhibitor of inducible nitric oxide synthase, preferably aminoguanidine, to a mammalian host susceptible to pertussis in a small but effective amount for inhibiting the toxic effects of TCT released by *Bordetella pertussis*.

1 Claim, 3 Drawing Sheets

METHOD FOR THE TREATMENT OF PERTUSSIS WITH AMINOGUANIDINE

This invention was made with Government support under grant number AI 25584 awarded by the National Institutes of Health. The Government has certain rights in the invention.

BACKGROUND OF THE INVENTION

The present invention relates to a method for the treatment of pertussis.

Despite the availability of a highly effective vaccine, whooping cough (pertussis) remains a global problem and a persistent clinical challenge. Fears about vaccine safety have spawned recent epidemics in industrialized nations like Japan, Great Britain, and Sweden; even in the U.S., with vaccine acceptance approaching 95%, new estimates of the annual number of pertussis cases are as high as 125,000 (Sutter et al., JAMA 26-7, 386-391 (1992).]Much of pertussis research has centered on the development of an acellular vaccine with a lower side effect rate, but it is unlikely that the pertussis burden in well-vaccinated countries will decrease. Infants and children hospitalized with pertussis still must endure frequent violent coughing episodes that continue for weeks after antibiotics have eliminated the bacteria. Complications range from the encephalopathy (presumably from anoxia) to secondary pneumonia, the latter being the most frequent cause of pertussis-related mortality [Olson, *Medicine* 54, 427-469 (1975)]. Currently, there is no therapy to relieve the debilitating symptoms of pertussis, shorten its duration, or reduce the frequency of sequelae.

The causative agent of pertussis is *Bordetella pertussis* (and, less frequently, *B. parapertussis*), which specifically colonizes and then destroys the ciliated cells lining the large airways [Mallory et al., *J. Med. Res.* 27, 115-123 (1912)]. The consequences of this cytopathology are severe, since ciliary activity is normally the sole means of transporting mucus out of the respiratory tract. As mucus, multiplying bacteria, and inflammatory debris accumulate, coughing becomes the only remaining means of airway clearance.

Of the various toxins and virulence-related factors produced by *B. pertussis*, only one has been demonstrated to reproduce the specific respiratory tract cytopathology of the pertussis syndrome. That molecule is tracheal cytotoxin (TCT), a low molecular weight glycopeptide released by *B. pertussis* during normal growth.

It is known that the destruction of ciliated cells can be duplicated by TCT (Goldman et al., *Infect. Immun.* 36, 782-794 (1982)], and this toxin has been subsequently purified [Cookson et al., *Infect. Immun.* 57, 2223-2229 (1989)] and chemically characterized [Cookson et al., *Biochemistry* 28, 1744-1749 (1989)]. TCT is enzymatically processed from *B. pertussis* cell wall peptidoglycan and accumulates at micromolar levels in the culture supernatant during log-phase growth. It is a 921 dalton disaccharide-tetrapeptide and is illustrated in the accompanying FIG. 1.

BRIEF DESCRIPTION OF THE INVENTION

In accordance with the present invention, a method is provided for the treatment of pertussis. The method preferably comprises treating a mammalian host susceptible to pertussis with aminoguanidine in a small but effective amount for inhibiting the toxic effects of TCT released by *Bordetella pertussis*.

The peptidoglycan-derived structure of TCT identifies it as a member of the "muramyl peptide" family. Muramyl peptides are responsible for a wide variety of biological activities, including adjuvanticity, pyrogenicity, and somnogenicity. There are many similarities between the biological activities of muramyl peptides and those of the inflammatory mediator interleukin-1 (IL-1) [Dinarello and Krueger, *FASEB Journal* 45, 2545-2548 (1986)]. IL-1 may also be the central factor linking the pathology of pertussis to muramyl peptide effects, including immunopotentiation, fever, and sleep (Nixon et al., *Abst. Gen. Meet. Am. Soc. Microbiol.*, p. 61, abst. no. B-216 (1991)]. In these other activities, the responses to muramyl peptides have been correlated to the production of IL-1 as an intercellular mediator; in contrast,, as shown herein, muramyl peptides may also act directly on their target cells through induction of intracellular IL-1 activity. This mechanism represents a unique enlistment by B. pertussis of a natural host cytokine to trigger cell-specific pathophysiology.

One mechanism by which cytokines can cause macrophage-mediated destruction of target cells is through the production of nitric oxide (NO·) [Hibbs et al., *Science* 235, 473-476 (1987)]. NO· is a free radical derived from the guanidino nitrogen atom of L-arginine through the action of nitric oxide synthase (NOS). NO· complexes with iron in heme-containing proteins and in enzymes containing iron-sulfur centers; while this inhibits the activity of most such enzymes, one target, soluble guanylyl cyclase, is activated to produce high levels of CGMP. The rate limiting enzyme in DNA synthesis, ribonucleotide reductase, is another non-heme iron-containing enzyme that is a target of NO·. In addition No· can react with superoxide anion to form peroxynitrite, which decays to form highly reactive hydroxyl radical.

Cytokines have been shown to activate an inducible isoform of NOS that is distinct from the constitutive NOS responsible for effects on vascular tone and neurotransmission [Moncada et al., *Pharmacol. Rev.* 43, 109-142 (1991)]. This inducible NOS is implicated herein as a key element in TCT-triggered pathology. In accordance with the present invention, aminoguanidine, a selective inhibitor of inducible NOS (Corbett et al., *Diabetes* 41, 552-556 (1992)], is able to interfere with TCT (or IL-1) toxicity for respiratory epithelial cells. All of the results herein point to NO·-mediated damage for destruction of ciliated cells and for halting proliferation of HTE cells (perhaps through the inhibition of ribonucleotide reductase). Treatment with aminoguanidine greatly reduces the toxic effects of TCT.

It will be appreciated by the person skilled in the art that other selective inhibitors of inducible NOS can similarly be used in the method of the invention in place of aminoguanidine.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments taken in conjunction with the accompanying drawings in which:

BRIEF DESCRIPTION OF THE DRAWINGS

FIG. 3 is a graphical representation that shows, in four panels, the effect of aminoguanidine (AG) on hamster tracheal epithelial (HTE) cells treated with TCT or IL-1.

In order to further illustrate the invention, the following exemplary procedures were carried out with the results stated hereinbelow and as shown in the accompanying figures. It will be appreciated, however, that the invention is not limited to these examples or the details described therein.

EXAMPLES

Since there is evidence linking interleukin-1 (IL-1) to the other biological activities of muramyl peptides, it is believed that IL-1 may be involved in TCT-like effects. Therefore, assays were carried out for production of IL-1 in hamster trachea epithelial (HTE) cells and tracheal organ cultures treated with TCT. These assays were carried out in accordance with conventional published procedures cited hereinbelow.

Figure 1:
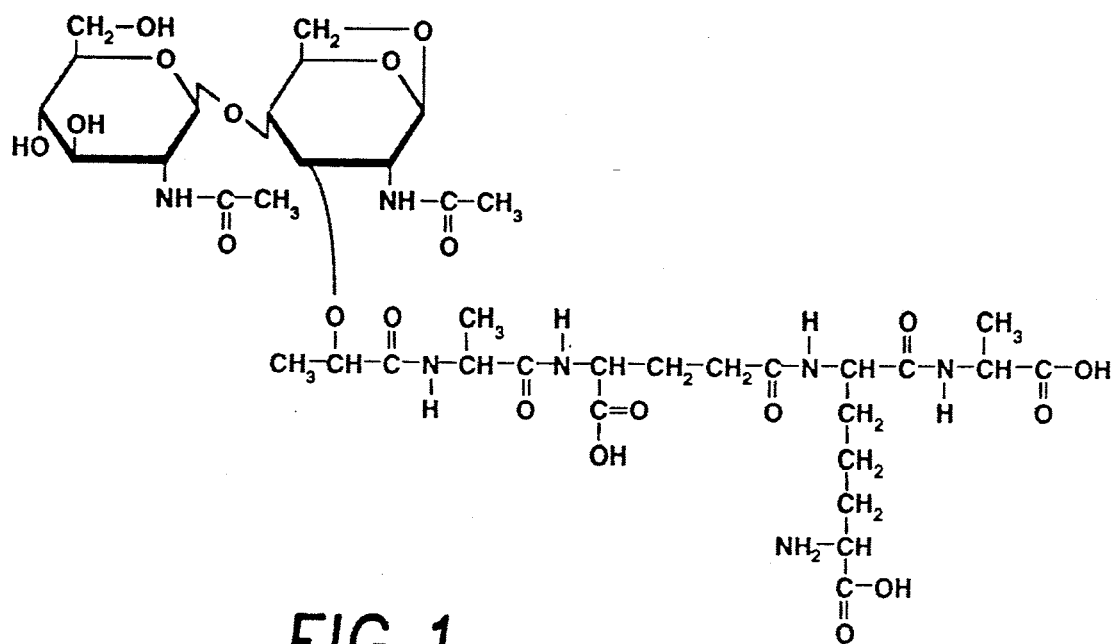
FIG. 1 shows the primary structure of *Bordetella pertussis* TCT, N-acetylglucosaminyl-1,6-anhydro-N-acetylmuramyl-L-alanyl-γ-D-glutamyl-meso-diaminopimelyl-D-alanine.
Figures 2A, 2B, 2C:
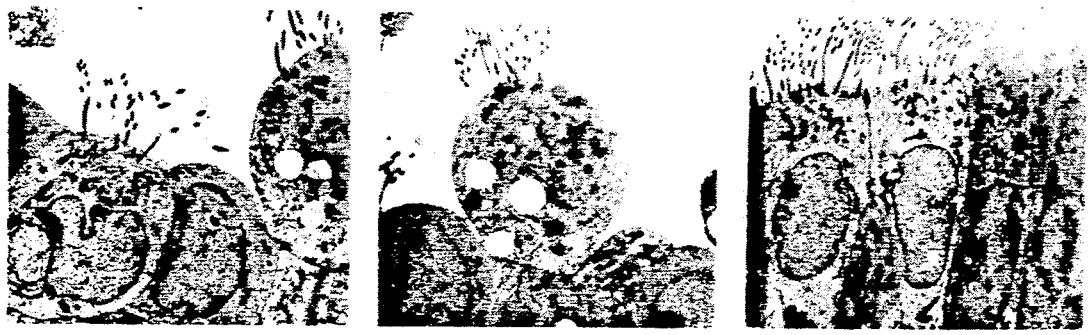
FIG. 2 is a photographic representation that shows, in three panels, the ciliated cell destruction in hamster tracheal organ cultures treated with TCT (FIG. 2A) or IL-1 (FIG. 2B) compared to the untreated control cells (FIG. 2C), each panel after 102 hours of treatment, and at X2,400.
Figure 3A:
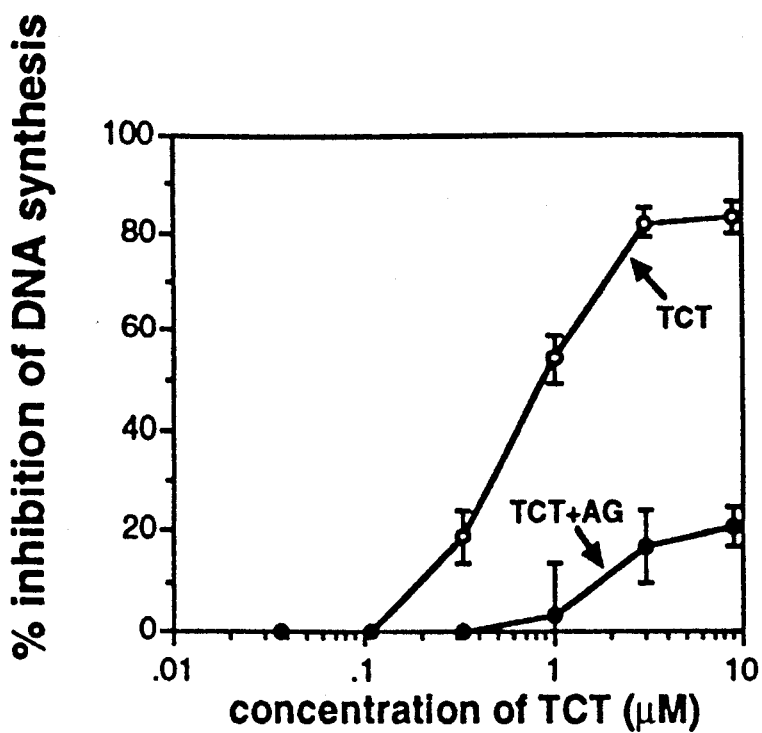
In FIGS. 3A and 3B, the % inhibition of DNA synthesis is plotted against concentration of either TCT in $\mu M$ (FIG. 3A) or IL-1 in ng/ml (FIG. 3B).
Figure 3B:
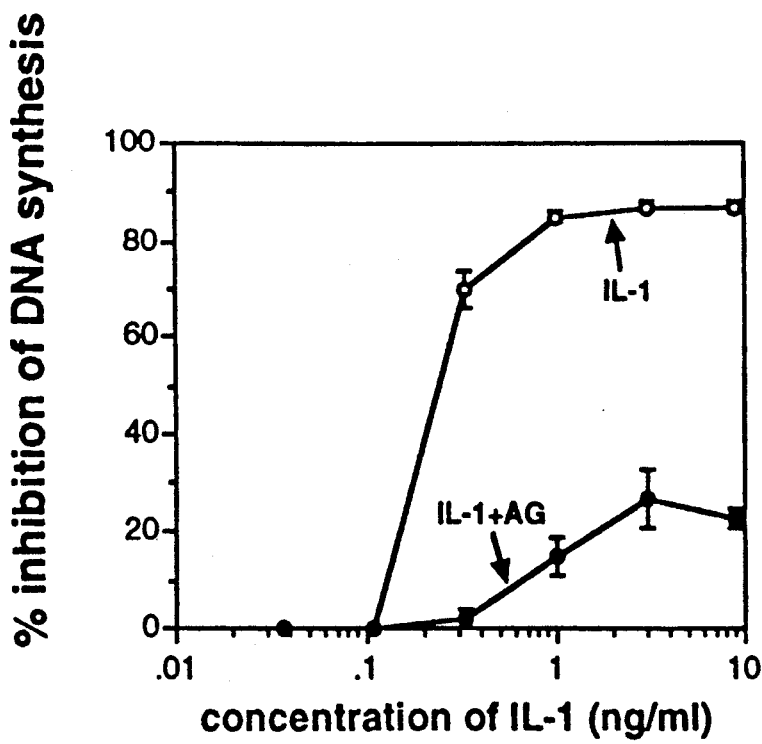
Figure 3C:
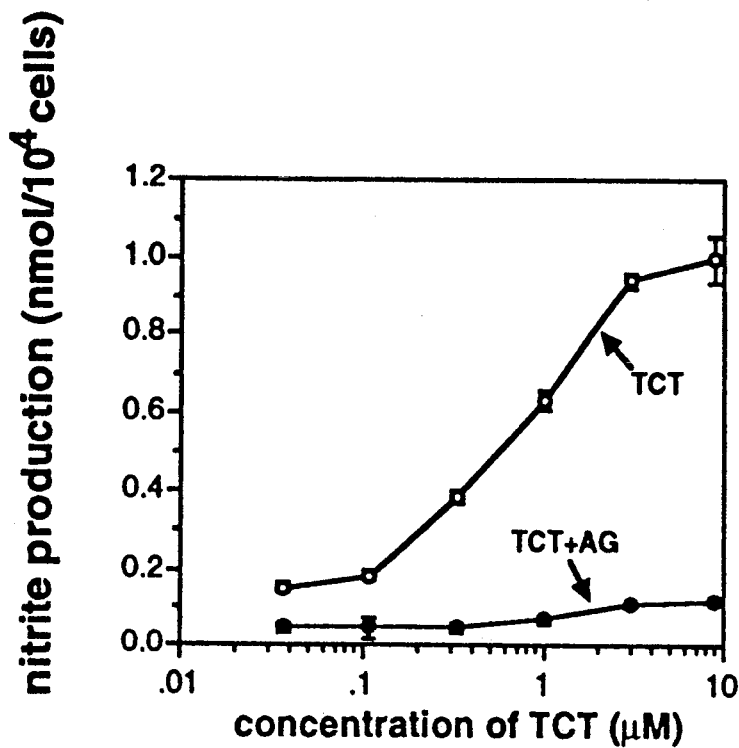
In FIGS. 3C and 3D, the nitrite production (nmol/$10^4$ cells) is similarly plotted as in FIGS. 3A and 3B against concentration of either TCT (FIG. 3C) or IL-1 (FIG. 3D).
Figure 3D:
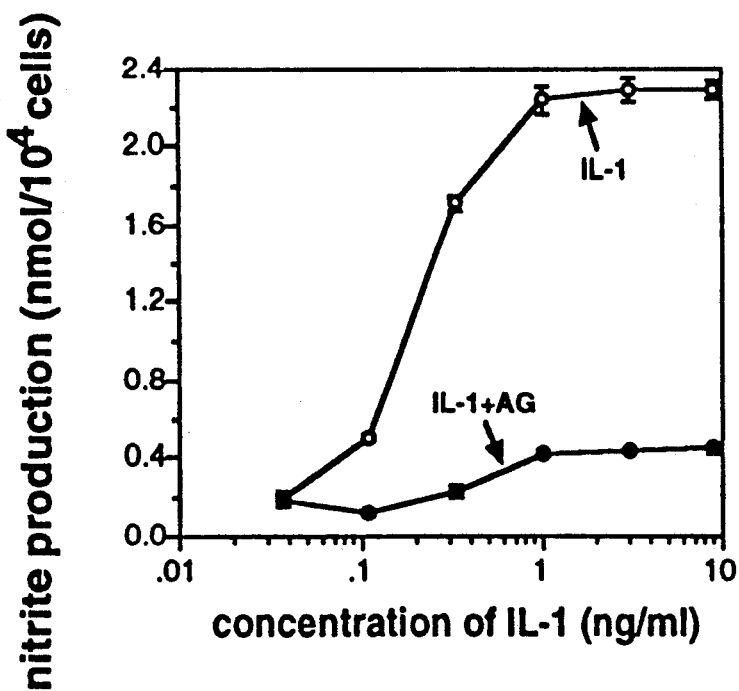

IL-1α was produced intracellularly in both systems, although it was not released into the culture supernatants. Furthermore, when recombinant murine IL-1 was added to HTE cells or to hamster tracheal organ cultures, all of the biological effects of TCT were manifested (see FIG. 2). Although a causal link remains to be established, these results suggest that TCT triggering of IL-1 production may be of central importance in the generation of cellular pathology [Nixon et al., *Abst. Gen. Meet. Am. Soc. Microbiol.*, p. 61, abst. no. B-216 (1991)].

IL-1 is known to trigger many intracellular pathways, and a number of these were investigated as possible mechanisms of cellular damage. Initial experiments pointed to TCT- and IL-1-triggered production of arachidonic acid metabolites and hydroxyl radicals; however, experiments with cyclooxygenase inhibitors and oxygen free radical scavengers failed to block TCT toxicity. IL-1 is also known to induce NOS; therefore, HTE cells were assayed for No, production using a colorimetric assay for its stable oxidation product, nitrite. As shown in FIG. 3, both TCT and IL-1 caused a dose-dependent increase in nitrite production that correlated well with inhibition of HTE cell DNA synthesis. Aminoguanidine (1 mill), a selective inhibitor of cytokine-inducible NOS (Corbett et al., *Diabetes* 41, 552–556 (1992)], abolished most of this nitrite production, confirming that the test was measuring NOS activity. Most importantly, aminoguanidine also eliminated most of the toxicity caused by TCT and IL-1. In tests with hamster tracheal organ cultures, another inhibitor of NOS, N-monomethyl-L-arginine (NMMA) [Hibbs et al., *J. Immunol.* 138, 550–565 (1987)] was used. The normal progression of TCT damage, as reflected by ciliostasis and extrusion of ciliated cells, was largely blocked by incubation with NMMA.

The in vitro model systems used herein for studying the effect of TCT and aminoguanidine on the hamster trachea epithelial (HTE) cell cultures and hamster tracheal organ cultures were carried out as follows:

I. Defining the respiratory epithelial pathology mediated by TCT

TCT was previously discovered and purified based on its ability to duplicate pertussis respiratory epithelial pathology in vitro, using hamster and human tissue [Cookson et al., *Infect. Immun.* 57, 2223–2229 (1989); Goldman et al., *Infect. Immun.* 36, 782–794 (1982); Wilson et al., *Infect. Immun.* 59, 337–345 (1991)]. These published model systems provide both quantitative and qualitative readouts on various aspects of damage in pertussis. For all work with these in vitro models, TCT was purified by solid-phase extractions and reversed phase HPLC [Cookson et al., *Infect. Immun.* 57, 2223–2229 (1989)], and the product was quantitated by amino acid analysis and checked for contaminating endotoxin using a chromogenic Limulus amebocyte lysate assay.

A. Hamster trachea epithelial (HTE) cell cultures

1. Inhibition of DNA synthesis. HTE cells are a proliferating, nontransformed, homogenous cell culture [Goldman et al., *In Vitro* 16, 313–319 (1980)], and this system provides the standard quantitative assay for TCT toxicity [Cookson et al., *Infect. Immun.* 57, 2223–2229 (1989); Goldman et al., *Infect. Immun.* 36, 782–794 (1982)]. Dose-response curves allow a quantitative assessment of relative biological activity, based on the concentration of TCT required to elicit half-maximal inhibition of $^3$H-thymidine incorporation [Luker et al., *Proc. Natl. Acad. Sci. USA* (in press) (1993)]. Because the cells are seeded and assayed in microtiter wells, dozens of samples can be titrated and compared in one experiment.

2. Stimulation of nitrite production. Nitrite is a stable oxidation product of nitric oxide, and it accumulates in the supernatants of HTE cells treated with TCT or IL-1. Quantitative nitrite measurement was made by a colorimetric assay based on reaction with the Griess reagent (Green et al., *Anal. Biochem.* 126, 131–138 (1982)]. This was easily coupled to the DNA synthesis assays described above, since each microtiter well culture supernatant can be transferred to new wells and nitrite levels determined with a spectrophotometric plate reader. Levels of nitrite production typically correspond to levels of DNA synthesis inhibition at each dose of TCT (see FIG. 3). Because all wells contain equal numbers of serum-synchronized cells, standardization between samples was not necessary. Confirmation that the values reflect NO· production came from controls with inhibitors of NOS.

B. Hamster tracheal organ cultures

1. Microscopic evaluation of damage. Hamster tracheal rings were used as the standard model to reflect genuine cytopathology caused by TCT, since ciliated cells are specifically damaged by this toxin. Visual assessment of the decline in ciliary activity and extrusion of ciliated cells was made over 3–5 days using an inverted microscope. In addition, histopathological sectioning and staining [Goldman et al., *Infect. Immun.* 36, 782–794 (1982)] at various time points verified the specificity for ciliated cells (see FIG. 3).

The aminoguanidine inhibitor of TCT toxicity described herein can be used for administration to warm blooded mammals by conventional means, preferably in formulations with pharmaceutically acceptable diluents and carriers. The amount of the active inhibitor to be administered must be an effective amount, that is, an amount which is medically beneficial but does not present toxic effects which overweigh the advantages which accompany its us&. It would be expected that the adult human daily dosage would normally range upward from about one milligram per kilo of body weight of the drug. A suitable route of administration is orally in the form of capsules, tablets, syrups, elixirs and the like, although parenteral administration also can be used, e.g. intravenously, intraperitoneally or subcutaneously. Intravenous administration of the drug in aqueous solution such as physiologic saline is illustrative. Intratracheal aerosol administration is another useful method of drug delivery and may result in fewer side effects because of more direct delivery to the affected tissue. This can be accomplished by an "inhaler" type of device such as that used by asthma patients for airway drug delivery. Appropriate formulations of the drug in pharmaceutically acceptable diluents and carriers in therapeutic dosage form can be prepared by reference to general texts in the field such as, for example, *Remington's Pharmaceutical Sciences*, Ed. Arthur Osol, 16th ed., 1980, Mack Publishing Co., Easton, Pa.

Various other examples of the invention will be apparent to the person skilled in the art after reading the present disclosure without departing from the spirit and scope of the invention and it will be understood that all such other examples are included within the scope of the appended claims.

What is claimed is:

1. A method for treatment of pertussis which comprises administering to a mammalian host an effective amount of aminoguanidine sufficient to inhibit the toxic effects of TCT released by *Bordetella pertussis*.

* * * * *